United States Patent [19]

Yoshinari et al.

[11] Patent Number: 4,728,672

[45] Date of Patent: Mar. 1, 1988

[54] PROCESS FOR PRODUCING HYDROCARBONS

[75] Inventors: Tomohiro Yoshinari; Fujio Suganuma, both of Saitama; Chikara Sera, Tokyo, all of Japan

[73] Assignee: Research Association for Petroleum Alternatives Development, Tokyo, Japan

[21] Appl. No.: 940,378

[22] Filed: Dec. 11, 1986

Related U.S. Application Data

[63] Continuation of Ser. No. 784,084, Oct. 4, 1985, abandoned.

[30] Foreign Application Priority Data

Oct. 8, 1984 [JP] Japan .................................. 59-211137
Jun. 28, 1985 [JP] Japan .................................. 60-141826

[51] Int. Cl.$^4$ ....................... C07C 27/00; C07C 27/06
[52] U.S. Cl. ..................................... 518/717; 518/714; 518/713; 518/715; 518/721; 585/733; 585/638; 585/469; 585/357
[58] Field of Search ............... 518/717, 714, 713, 715, 518/719, 721; 585/733, 638, 469, 357

[56] References Cited

U.S. PATENT DOCUMENTS

| | | | |
|---|---|---|---|
| 3,254,023 | 5/1966 | Minle et al. | 518/717 |
| 3,842,121 | 10/1974 | Ichikawa et al. | 518/717 |
| 4,151,190 | 4/1979 | Murchison et al. | 518/717 |
| 4,199,522 | 4/1980 | Murchison et al. | 518/717 |
| 4,206,134 | 6/1980 | Kugler et al. | 502/185 |
| 4,385,193 | 5/1983 | Bijwaald et al. | 585/638 |

FOREIGN PATENT DOCUMENTS 6734583 4/1983 Japan .
4842484 3/1984 Japan .

Primary Examiner—Helen M. S. Sneed
Assistant Examiner—Chung K. Pak
Attorney, Agent, or Firm—Sughrue, Mion, Zinn, Macpeak, and Seas

[57] ABSTRACT

A process for producing hydrocarbons which comprises bringing a gas mixture comprising hydrogen and carbon monoxide into contact with a catalyst comprising manganese oxide, alkali metal, sulfur, and ruthenium to produce hydrocarbons. The hydrocarbons formed are rich in olefins. When a catalyst prepared by combining the above described catalyst with crystalline zeolite is used, the hydrocarbons formed becomes rich in liquid hydrocarbons, particularly, a gasoline fraction.

17 Claims, No Drawings

PROCESS FOR PRODUCING HYDROCARBONS

This is a continuation of application Ser. No. 784,084 filed Oct. 4, 1985 which is now abandoned.

FIELD OF THE INVENTION

The present invention relates to a process for effectively producing hydrocarbons, particularly those rich in olefinic hydrocarbons and liquid hydrocarbons, from a gas mixture composed of hydrogen and carbon monoxide (hereinafter, referred to as synthesis gas).

BACKGROUND OF THE INVENTION

It is known to produce hydrocarbons by bringing a gas mixture composed of hydrogen and carbon monoxide into contact with a catalyst at an elevated temperature under pressure, as the synthesis of hydrocarbons by the so-called Fischer-Tropsch (FT) process.

The catalytic hydrogenation of carbon monoxide yields a mixture composed of paraffins and olefins having from 1 to 40 carbon atoms, depending upon the catalyst used, and the reaction conditions applied, and it sometimes yields compounds containing oxygen such as alcohol, aldehyde, ketone, ester, or aliphatic acid. Further, under specific synthetic conditions, a small amount of aromatic hydrocarbons is formed.

Remarkable activity for hydrogenation of carbon monoxide is shown by Periodic Group VIII elements, particularly, iron, cobalt, nickel and ruthenium. Even though these elements are used, distributions of the products and compositions thereof vary remarkably, depending upon the kind and the amounts of the elements. It is already known that nickel, cobalt, and ruthenium type catalysts produce mainly a mixture of unbranched saturated hydrocarbons, and that hydrocarbons containing unsaturated aliphatic compounds and oxygen-containing compounds, particularly aliphatic primary alcohols, can be produced using an iron-containing catalyst.

However, the iron type catalysts produce a mixed product rich in unsaturated hydrocarbons, but amounts of carbon dioxide gas and oxygen-containing compounds formed as by-products are large, and selectivity of hydrocarbons is inferior. On the other hand, the ruthenium type catalysts have a high FT reaction activity which is several times higher than that of the iron type catalysts, but they produce a product having a larger amount of saturated hydrocarbons, and have high dependence on the reaction pressure and reaction temperature, and there is a tendency that the chain growth probability: $\alpha$ value of Schultz-Flory law, which is often used as an index of FT reaction, greatly decreases with increases of the reaction temperature. For such a reason, it has been said that it is very difficult to selectively produce a reaction product containing a large amount of olefinic hydrocarbons using the ruthenium type catalyst. Further, since the iron type catalysts used in the known processes have low reaction activity, iron content per unit catalyst is large, and the reaction is carried out at a high temperature. Carbon monoxide forms carbon at a high reaction temperature according to Boudouard's equilibrium. Deposition of the carbon causes deactivation of the catalyst and destruction of the catalyst structure; consequently, the catalyst life is remarkably reduced. Further, since the iron content is high, there is a problem in that a sintering phenomenon occurs to a significant extent, and the useful life of the catalyst is unsatisfactory.

Catalysts for hydrogenating carbon monoxide ordinary used are sensitive to poisoning, most particularly with respect to sulfur compounds. Therefore, it is necessary to purify the raw materials of carbon monoxide and hydrogen, and thus it is urgently required to develop a sulfur resisting catalyst considering economy of the process. Further, in the case of producing olefins by hydrogenating carbon monoxide, though a higher conversion can be attained with increase of hydrogen partial pressure, hydrogenation of the olefins formed is accelerated at the same time, to result in deterioration of olefin selectivity for the product. Moreover, it is more difficult to increase the production ratio of ethylene/ethane than to increase the production ratio of propylene/propane, in the viewpoint of equilibrium in the FT reaction.

In recent years, a conversion process for selectively obtaining liquid hydrocarbons, and particularly a gasoline fraction from a synthesis gas, which comprises using zeolite and a carbon monoxide reduction catalyst (FT synthetic catalyst and methanol synthetic catalyst) in combination has been studied.

This conversion process includes a two-stage conversion process wherein the reactions are carried out in different reactors, and a one-stage process wherein a catalyst comprising a metal component active to reduction of carbon monoxide supported on specified zeolite is used or a mixed catalyst which is a physical mixture of a carbon monoxide reduction catalyst and a specified zeolite is used.

The one-stage process is generally expected to be a more economic process than the two-stage process, because the process is simplified. However, satisfactory results in reaction activity or distribution or composition of the formed hydrocarbon product are not obtained in the one-stage process, because the optimum conditions (particularly, reaction temperature and pressure) for the two catalysts are different from each other, as compared with the two-stage process wherein the carbon monoxide reduction catalyst and the zeolite catalyst can be used under the optimum conditions, respectively. For example, processes for selectively producing a gasoline fraction in one stage using a ruthenium-containing catalyst of this kind are known in U.S. Pat. No. 4,157,338 and Japanese Patent Application (OPI) Nos. 19386/83, 127784/83, and 192834/83 (the term "OPI" as used herein refers to a "published unexamined Japanese Patent Application open to public inspection"). However, these processes have disadvantages in that the amount of methane formed is large and yield of the gasoline fraction is low, conversion of carbon monoxide is low and/or high reaction pressure is required.

As is described above, it is very difficult to selectively produce hydrocarbons of the specified useful component or the specified gasoline fraction by the prior processes, because undesirable methane or carbon dioxide gas is formed in a relatively large amount as the by-product, selectivity for the desired hydrocarbons is low, and carbon atom distribution of the formed hydrocarbons is very broad and hydrocarbons in a range of gas to wax are formed.

SUMMARY OF THE INVENTION

It has now been found that ruthenium type carbon monoxide reduction catalysts containing alkali metal and sulfur together with manganese oxide show unique behavior in that they have excellent performance in the formation of hydrocarbons rich in olefin in a contact reaction (carbon monoxide reduction reaction) between carbon monoxide and hydrogen. Furthermore, when this carbon monoxide reduction catalyst is combined with zeolite, it shows an excellent performance in converting the reaction product rich in olefin into liquid hydrocarbons, particularly hydrocarbons rich in the gasoline fraction. Thus, the present invention have been completed. The excellent performances of the catalysts used in the present invention in production of the specified hydrocarbon components is believed to be based on the oxidation number or crystal structure of the manganese oxide composing the catalyst as described later in examples and comparative examples, and, at the same time, based on the coexistence of the alkali metal and the sulfur component contained together therewith.

One object of the present invention is to provide a process for producing hydrocarbons, particularly hydrocarbons rich in olefinic hydrocarbons or liquid hydrocarbons in good selectivity.

Another object is to provide a process for producing the desired hydrocarbons in good selectivity while preventing formation of methane.

A further object is to provide a process for producing the desired hydrocarbons in good conversion.

Accordingly, the present invention is a process for producing hydrocarbons which comprises bringing a gas mixture comprising hydrogen and carbon monoxide into contact with a catalyst comprising manganese oxide, alkali metal, sulfur, and ruthenium to produce hydrocarbons.

DETAILED DESCRIPTION OF THE INVENTION

The catalysts used in the present invention are those wherein ruthenium is supported on manganese oxide, and alkali metal and sulfur component are contained therein, and they may contain, if desired, crystalline zeolite or other inorganic metal oxides, composite oxides, or activators.

Since the crystalline zeolite has no ability for reducing carbon monoxide, the terminology "carbon monoxide reduction catalyst" used in the present specification means a composition of catalyst components other than crystalline zeolite.

These catalyst components may be incorporated in any order. With respect to the carbon monoxide reduction catalyst, for example, alkali metal, sulfur component, a carrier substance and an activator may be mixed with manganese oxide and then ruthenium is supported on the resulting mixture, or alkali metal, sulfur component, a carrier and an activator may be supported on manganese oxide likewise ruthenium. Alternatively, the above-described carrier substance may be a physical mixture, with a mixture of manganese oxide, alkali metal, sulfur, and ruthenium, or the carrier substance may support the other catalyst components. Preferable catalysts are those wherein manganese oxide or a mixture of manganese oxide and a carrier substance supports the other catalyst components and those wherein the carrier substance supports the other catalyst components. As processes for preparation, it is possible to utilize various known technique, such as impregnation on manganese oxide, or gel mixing or dry mixing in case of synthesizing manganese oxide, etc.

The crystalline zeolite may be incorporated in the carbon monoxide reduction catalyst in any stage of preparation of the catalyst, and it may be used as a mixture prepared by mixing with the prepared carbon monoxide reduction catalyst. In the case of incorporating the crystalline zeolite in preparation of the carbon monoxide reduction catalyst, the catalyst may be prepared by mixing the crystalline zeolite with manganese oxide or the carrier substance and, thereafter, supporting ruthenium and the other catalyst components on it or may be prepared by supporting crystalline zeolite on manganese oxide or a carrier substance, together with ruthenium and the other catalyst components. In the case of incorporating crystalline zeolite in the carbon monoxide catalyst which has been prepared, the catalyst may be prepared, for example, by mixing the crystalline zeolite with the carbon monoxide reduction catalyst, or by additionally adding a carrier substance to the mixture. Preferred catalysts are those prepared by incorporating crystalline zeolite in the carbon monoxide reduction catalyst which has been prepared.

In the following, each of the catalyst components is illustrated. Firstly, the carbon monoxide reduction catalyst is illustrated.

Manganese oxide used for preparation of the catalyst can be various types of manganese oxide. Manganese oxide as used here includes oxides such as $MnO_2$, $Mn_2O_3$, $Mn_3O_4$, $MnO$, etc. These oxides may have various crystal structures. For example, as $MnO_2$, those having crystal structure of the $\alpha$, $\beta$, $\gamma$, $\delta$ or $\epsilon$-type are used, and an $Mn_2O_3$, those having crystal structure of $\alpha$ or $\gamma$-type are used. The amount of manganese oxide in the carbon monoxide reduction catalyst is preferred to be in a range of from about 10 to 99.8 wt %, and preferably particularly from about 60 to 99.8 wt %.

In order to improve the dispersed state of the ruthenium and to keep reactivity high, it is advantageous that the surface area of the manganese oxide is large. Further, from the viewpoint of utilizing the redox reaction of manganese oxide, in order to improve catalytic activity and to selectively obtain the desired hydrocarbon component, it is preferred to use those manganese oxides wherein the average charge number of manganese is in a highly oxidized state, namely, those containing a larger amount of charge component of $Mn^{4+}$ or $Mn^{3+}$ ($MnO_2$, $Mn_2O_3$, etc.).

As methods of supporting alkali metal (e.g., lithium, sodium, potassium, cesium or rubidium) and the sulfur component on the manganese oxide, it is possible to use conventional impregnation techniques of supporting which comprise bringing manganese oxide into contact with a solution containing an alkali metal compound or a sulfur compound, for example, by immersing manganese oxide in a solution of an alkali metal compound or a sulfur compound to adsorb on manganese oxide, by allowing to adhere on manganese oxide by ion-exchange, by evaporating the solution containing manganese oxide till dryness, or by dropwise adding the solution onto manganese oxide. Supporting of the alkali metal and the sulfur component can be carried out before or after the supporting of the ruthenium or simultaneously with the supporting of the ruthenium, but it is preferred that the alkali metal and the sulfur components are supported prior to supporting of ruthenium.

Examples of alkali metal compounds capable of using in these cases include alkali metal hydroxides such as LiOH, NaOH, KOH, CsOH, RbOH, etc., alkali metal carbonates such as $Li_2CO_3$, $Na_2CO_3$, $K_2CO_3$, $Cs_2CO_3$, Rb$_2$CO$_3$, etc., inorganic salts of alkali metal such as halides, nitrates, etc., organic salts of alkali metal such as acetates, etc., alcoholates and other various alkali metal compounds. Examples of sulfur compounds include thiocyanates, sulfates, hydrogen sulfates, pyrosulfates, sulfites, hydrogen sulfites, thiosulfates, sulfides, polysulfides, etc., of various metals or ammonium cation, sulfur containing hydrocarbons, sulfuric acid esters, etc.

The sulfur component may be added to a catalyst conposition in which catalyst components other than the sulfur component have been incorporated. For example, it is possible to add the sulfur component to the catalyst by supplying sulfur in the state of being a sulfur compound, e.g., as gaseous sulfur compounds, e.g., hydrogen sulfide, carbon disulfide, carbonyl sulfide, etc., or sulfur-containing hydrocarbons, etc., through the prepared catalyst, preferably, the prepared catalyst charged in a reactor.

Addition of the alkali metal component and the sulfur component may be carried out at any time during preparation or after preparation of manganese oxide, and before, after, or during supporting Ru as active metal. In case of using H$_2$S, CS$_2$, etc., addition of the sulfur can be carried out after reduction of the catalyst (after combination with crystalline zeolite) or during the carbon monoxide reduction reaction.

Addition of the alkali metal and the sulfur may be carried out in any order. Further, the alkali metal and the sulfur can be added at the same time by dissolving a compound containing both the alkali metal and the sulfur component, e.g., alkali metal sulfide, sulfur-containing acid salts of alkali metal (examples in the case of using potassium compounds include K$_2$SO$_4$, K$_2$S$_2$O$_7$, K$_2$S, K$_2$S$_5$, K$_2$SO$_3$, KHSO$_3$, K$_2$S$_2$O$_3$, KSCN, KHSO$_4$, etc.), etc., in a suitable solvent.

Alternatively, desired amounts of alkali metal and the sulfur component may be incorporated in the case of synthesizing manganese oxide. For example, it may be carried out by a process which comprises incorporating alkali metal in case of synthesizing $\alpha$-type MnO$_2$ by electrolytic oxidation, or by a process which comprises washing with water so as to remain a suitable amount of alkali metal or sulfate radical in case of synthesizing $\gamma$-type MnO$_2$ by air oxidation of manganese carbonate.

Preferred carbon monoxide reduction catalysts of the present invention are those wherein ruthenium is supported on manganese oxide containing small amounts of alkali metal and sulfur.

The preferred amount of alkali metal to be incorporated is generally in a range of from about 0.01 to 8 wt %, and preferably from 0.05 to 6 wt % (calculated as metal), based on the total weight of the carbon monoxide reduction catalyst. The preferred amount of sulfur to be incorporated is in a range of from about 0.001 to 3 wt %, and preferably from 0.07 to 1.5 wt % (calculated as S), based on the total weight of the carbon monoxide reduction catalyst. If the amount of either the alkali metal or the sulfur component is too small in the catalyst, the desired hydrocarbon component cannot be selectively obtained, and temperature dependence of distribution of the product becomes high. If the amount of one component thereof is too large, significant improvement of catalytic activity is not obtained.

Other sparingly soluble substances which do not substantially damage the hydrocarbon synthesizing characteristic of ruthenium-containing catalysts can be incorporated in the catalyst as carrier substances. For example, it is possible to mix inorganic metal oxides such as TiO$_2$, SiO$_2$, Al$_2$O$_3$, Cr$_2$O$_3$, V$_2$O$_5$, WO$_3$, MoO$_3$, etc., or natural clay minerals with manganese oxide. It is also possible to mix such metal oxides or clay minerals with manganese oxide containing alkali metal and sulfur, to mix them with manganese oxide containing alkali and sulfur which supports ruthenium, or to support them on another carrier. Further, it is possible to support desired amounts of manganese oxide, alkali metal, sulfur, and ruthenium on these carrier substances. A preferred amount of the above described carrier substances to be incorporated is in a range of from about 0.01 to 90 wt %, and particularly preferably from about 5 to 60 wt %, based on the whole weight of the carbon monoxide reduction catalyst. These carrier substances are effective for increasing the surface area of the catalyst, increasing mechanical strength, improving molding property, improving removal of reaction heat or reducing the price of the catalyst.

Supporting of ruthenium on the mixture of manganese oxide, alkali metal, and sulfur can be carried out by utilizing conventional impregnation techniques for supporting a substance, which comprises bringing the above described mixture into contact with a solution containing a ruthenium compound, for example, by immersing the above described mixture in a solution of a ruthenium compound to adsorb on the mixture, by allowing to adhere on the mixture by ion-exchange, by depositing on the mixture by adding precipitants such as alkalis, by evaporating the solution containing the mixture till dryness, or by dropwise adding the solution onto the mixture. Examples of ruthenium compounds capable of use in such cases include those soluble in water, such as ruthenium chloride, ruthenium nitrate, ruthenium acetate, ruthenium hexaammonium chloride ((Ru(NH$_3$)$_6$)Cl$_{13}$), etc., and those soluble in organic solvents, such as ruthenium carbonyl clusters, ruthenium acetylacetonate (Ru(C$_5$H$_7$O$_2$)$_3$), etc.

The amount of ruthenium to be incorporated is generally in a range of from about 0.1 to 50 wt %, preferably from about 0.1 to 30 wt %, and most preferably from 0.5 to 25 wt % (calculated as Ru), based on the total weight of the carbon monoxide reduction catalyst. If the amount of ruthenium to be incorporated is too small, catalytic activity becomes low, and if it is too large, selectivity for producing the desired hydrocarbon component deteriorates. Ruthenium in the catalyst is generally in a state such that the greater part is simple substance of metal (i.e., metallic state), but it may be in a state of a compound such as oxide.

Addition of ruthenium is not restricted to the above case of adding to the mixture of manganese oxide, alkali metal, and sulfur, and it is possible to incorporate ruthenium in a produced mixture after the above described mixture is combined with crystalline zeolite.

Further activators may be incorporated in the catalyst in order to increase activity. Examples of the activators include magnesium, zinc, copper, iron, etc., which may be incorporated in the catalyst in a state of simple substance of metal or a state of compound such as chloride, ammonium salt, nitrate, oxide, etc. Examples of activator component used as raw materials when preparing the catalyst include magnesium chloride, zinc chloride, copper chloride, iron chloride, iron nitrate, etc. The amount of the activator to be incorporated is preferred to be in a range of from about 0.01 to 35 wt %, and particularly preferably from about 0.1 to 20 wt % (calculated as metal), based on the total weight of the carbon monoxide reduction catalyst. A preferred sum total amount of the activator and the carrier substance is in a range of from about 0.01 to 90 wt % (base on the total weight of the carbon monoxide reduction catalyst). The activator may be added in case of synthesizing manganese oxide or may be mixed with manganese oxide, but it is preferred to add before or after supporting ruthenium after synthesizing manganese oxide, or simultaneously with supporting ruthenium. The activator can be added not only at preparation of the carbon monoxide reduction catalyst but also to the composite of the carbon monoxide reduction catalyst after preparation thereof.

In the following, the above described crystalline zeolite is illustrated.

Zeolite used as the crystalline zeolite in the present invention includes crystalline aluminosilicates, crystalline silicates synthesized by replacing a part or the whole of aluminium atoms in crystalline aluminosilicate with other metals, for example, trivalent metals such as iron, chromium, vanadium, bismuth, lanthanum, cerium, titanium, boron, gallium, etc. and crystalline silicates composed of 90 wt % or more of silica which hardly contain aluminium atoms. These crystalline zeolites may be any of H type zeolites, wherein the cation capable of carrying out ion-exchange is hydrogen, zeolites wherein a part or all of the hydrogen is exchanged for alkali metal such as Li, Na, K, Rb, Cs, etc., or alkaline earth metal such as Ca, Ba, Mg, Sr, etc., and zeolite containing these metals.

Examples of these crystalline zeolites include erionite, offretite, and ferrierite, which have a pore diameter of about 5 Å, faujasite type zeolite X or Y and mordenite type zeolite, which have a pore diameter of about 9 Å, and ZSM series zeolite which has an intermediate pore in a range of from about 5 to 9 Å of pore diameter, and has a ratio of silica to alumina of about 10/1 or more. These crystalline zeolites have been described in detail in *Saikin no zeolite gijutsu to oyo no shinpo sogoshiryoshu*, pages 46–57, published by Nippon Gijutsukeizai Center Shuppanbu, Jan. 11, 1982; *Zeolite*, pages 29–32 and 46–47, edited by Hiroshi Takahashi et al, published by Kodansha Co., Feb. 1, 1975; and Japanese Patent Application (OPI) No. 70828/82.

Of these zeolites, the most suitable zeolites for obtaining the gasoline fraction in a high yield are zeolites having a pore diameter of from 5 to 9 Å. Zeolites of this kind include ZSM series zeolites having a molar ratio of silica to alumina of 10/1 or more, such as ZSM-5, ZSM-11, ZSM-12, ZSM-21, ZSM-35, ZSM-38, etc., which were developed by Mobil Oil Corp., zeolites composed of silica-iron-alumina showing a X-ray diffraction pattern analogous to ZSM-5 which were developed by Shell International Research Co., ZSM-5 type crystalline zeolites which are produced by a different process from that of ZSM-5 but have the same X-ray diffraction pattern as that of ZSM-5, zeolites wherein a part or the whole of aluminum in the above described zeolites are replaced with other trivalent metals, and those wherein a part or the whole of H-type zeolites are replaced with alkali metal or alkaline earth metal by ion-exchanging.

The crystalline zeolites generally contain sodium, potassium or organic nitrogen cations as cations capable of carrying out ion-exchange. However, in case of using them for the conversion reaction of the present invention, it is preferred that at least 50% of these cations are replaced with hydrogen ions, alkaline earth ions, rare earth ions, transition metal ions, etc., so that acid sites appear. Generally, the cation exchange processing can be carried out by the known ion-exchange art which comprises processing with an aqueous solution containing cations for exchanging.

Further, crystalline zeolites containing organic nitrogen cations or ammonium ions can be easily converted into hydrogen ion type by heating at a range of 400° to 700° C. in the air to decompose and calcine the organic nitrogen cations or ammonium ions.

Combination of the above described carbon monoxide reduction catalyst and the crystalline zeolite can be carried out by processes known hitherto. Examples include a process which comprises physically mixing the carbon monoxide reduction catalyst with the crystalline zeolite to form a homogeneous mixture, a process wherein the former part of the reactor is filled with the carbon monoxide reduction catalyst and the latter part thereof is filled with the crystalline zeolite, and a process wherein the reactor is filled with the carbon monoxide reduction catalyst and the crystalline zeolite one after another so as to be present in multilayers. Further, a two-stage process wherein the carbon monoxide reduction catalyst and the crystalline zeolite are charged in different reactors, respectively, can be used, too. The carbon monoxide reduction catalyst, the crystalline zeolite, and the catalyst composition composed of both of them may have any desired shape, for example, powder, granules, extrusion moldings, etc. In order to improve molding property or for removal of reaction heat, the above described carrier substances may be added. The rate of the carbon monoxide reduction catalyst in the catalyst composition is from about 5 to 95 wt %, and preferably from about 30 to 80 wt %, based on the total amount of carbon monoxide reduction catalyst and crystalline zeolite. If the rate of the carbon monoxide reduction catalyst is too small, yield of the desired hydrocarbons is reduced. If the rate of the crystalline zeolite is too small, it becomes difficult to obtain the desired liquid hydrocarbons such as gasoline having a high octane value and excellent quality, kerosene, or gas oil in a good yield.

The carbon monoxide reduction catalyst containing manganese oxide, alkali metal, sulfur and ruthenium as essential components, the crystalline zeolite, or the catalyst composition obtained by combining both of them, produced as described above, is dried after molding by a conventional manner or without molding. The drying can be carried out by holding at room temperature to 300° C. for about 10 to 48 hours. The most suitable drying process is that which comprises heating in air at about 90° to 110° C. for few hours after drying at room temperature, or immediately heating in air at about 90° to 110° C. for few hours. The dried catalyst composition may be calcined by a conventional manner, as occasion demands.

In the process of the present invention, the carbon monoxide reduction catalyst free from crystalline zeolite and comprising ruthenium, alkali metal, sulfur, and manganese oxide, which is used in case of obtaining hydrocarbons rich in olefins as the desired product causes variation of distribution of the product, if it is calcined or not in the air at a certain elevated temperature prior to reduction by a hydrogen gas and introduction of a synthesis gas. In the case of obtaining hydrocarbons rich in $C_2$ to $C_4$ lower olefins, it is preferred that the calcining processing in the air is omitted, and it is introduced directly into a reduction step using a $H_2$ gas. In the case of obtaining hydrocarbons rich in high boiling point olefins, for example, olefins having from 5 to 40 carbon atoms, it is calcined at a temperature of about 600° C. or less, and preferably at from about 300° to 600° C. The calcining time is preferred to be in a range of from about 30 minutes to 24 hours. The calcining may be carried out by any manner of calcining only the substrate for supporting ruthenium prior to supporting ruthenium, calcining the catalyst after supporting ruthenium, or calcining the substrate for supporting ruthenium together with the catalyst. However, the most preferred manner is to calcine after supporting ruthenium. If calcining is carried out at a high temperature condition of above 600° C., the catalytic activity deteriorates and the selectivity for formation of olefins deteriorates.

In the process of the present invention, the composite catalyst composed of the carbon monoxide reduction catalyst comprising ruthenium, alkali metal, sulfur, and manganese oxide, and crystalline zeolite, which is used in case of obtaining hydrocarbons rich in liquid hydrocarbons as the desired product, does not cause great variation of distribution of the product if it is calcined or not prior to use for the reaction.

The calcining is preferably carried out at a temperature of from 150° to 600° C., and more preferably at from about 300° to 600° C., for from about 30 minutes to 48 hours. Drying or calcining may be carried out in any stage of preparation of the carbon monoxide reduction catalyst.

The catalyst composition prepared as described above is preferably subjected to reduction treatment in a reducing atmosphere such as hydrogen or carbon monoxide at a temperature of about 300° C. or more, preferably about 400° C. or more, for about 0.5 to 4 hours, prior to applying a synthesis gas. In this case, it is preferred to keep the system under an atmospheric pressure of about 1 atm. In the case of carrying out reduction processing with hydrogen, etc., the catalyst may be subjected to surface processing by a pre-treatment step wherein an oxygen-containing compound such as water, methanol, ethanol, etc., or hydrogen sulfide is introduced together with hydrogen, etc., to carry out activation and sulfurization, by which it becomes possible to control distribution of the product.

With respect to reaction operating conditions for the process of the present invention, the pressure is generally in a range of 0 to 100 kg/cm$^2$G (gauge pressure), preferably from 0 to 30 kg/cm$^2$G, and most preferably from 0 to 20 kg/cm$^2$G. The reaction may be carried out under reduced pressure. The temperature is in a range of from about 100° to 500° C., preferably from about 200° to 450° C., and most preferably from about 250° to 400° C. The molar ratio of hydrogen to carbon monoxide ($H_2/CO$) is in a range of from about 0.1/1 to 10/1, and preferably from about 0.5/1 to 4/1, and most preferably 0.5/1 to 1/1, which means that the gas mixture contains carbon monoxide in a slightly excess amount. The space velocity (GHSV) of the feed gas is in a range of from about 100 hr$^{-1}$ to 20000 hr$^{-1}$. The whole or a part of the gas mixture exhausted from the reactor is recycled to the apparatus after the formed hydrocarbon product is removed.

The catalyst used in the process of the present invention is generally applied as a fixed bed. However, it can be applied to a fluidized bed and a suspension bed wherein it is used in a finely divided state. Further, the catalyst may be removed from the reactor in order to regenerate continuously or discontinuously. Regeneration of the catalyst is carried out by burning it with the air in a special container to remove impurities attaching to the surface of the catalyst, and subsequently reducing it by a known method stated above.

It is believed that, in the reduction step of the pre-treatment of the catalyst or during the reaction, the greater part of the ruthenium compound in the catalyst becomes a simple substance of metal, and a part thereof becomes sulfide or oxide. Further, it is believed that, the initial form of manganese oxide in preparation of the catalyst, is converted into another crystal form or another manganese oxide during the reaction. In the catalyst of the present invention, ruthenium and manganese oxide are believed to act as a composite catalyst, and alkali metal and sulfur are believed to act as a promotor.

In the process of the present invention, hydrocarbons rich in unsaturated hydrocarbons are selectively formed from carbon monoxide and hydrogen when the catalyst used is a carbon monoxide reduction catalyst composed of sparingly soluble manganese oxide wherein alkali metal and sulfur are coexistent and ruthenium. Particularly, hydrocarbons rich in gaseous lower olefins are selectively obtained in a good yield under a reaction pressure of 0 to 5 kg/cm$^2$G using a catalyst which is not subjected to calcining processing, and hydrocarons rich in higher unsaturated hydrocarbons are selectively obtained in a good yield under a reaction pressure of about 5 Kg/cm$^2$G or more using a catalyst which is subjected to calcining processing. In the process of the present invention, though distribution of the formed hydrocarbon compounds follows the Schultz-Flory law with respect to $C_3$ or more fractions, the amount of methane formed, which is inevitable in the carbon monoxide reduction reaction using a conventional ruthenium type catalyst, is extremely small, and hydrocarbons rich in $C_2$ or more unsaturated hydrocarbons are obtained in a good yield. Further, since the catalyst of the present invention has good sulfur resistance, feed gases containing sulfur components as impurities can be used.

When the catalyst composed of the above described carbon monoxide reduction catalyst and crystalline zeolite is used in the process of the present invention, olefins formed by the carbon monoxide reduction catalyst are secondarily converted, and consequently liquid hydrocarbons, and particularly hydrocarbons comprising a gasoline fraction as a main component, can be obtained from the synthesis gas in a high selectivity and a high yield. Since the resulted gasoline fraction has a high aromatic hydrocarbon content, it can be used as fuel for cars having a high octane value or as petrochemical raw material. Further, since this catalyst also has good sulfur resistance, feed gasses containing sulfur components as impurities can be used.

In the following, the present invention is illustrated with reference to examples. In the following examples, the molar ratio of $H_2/CO$ in the reaction conditions was 1.0/1 unless otherwise stated.

$MnO_2$, $MnO$, $Mn_2O_3$ and $Mn_3O_4$ used were those available on the market unless otherwise stated. A portion of δ-type and a portion of β-type $MnO_2$ was produced according to the following reference example. In the case of using such $MnO_2$ obtained according to reference example, it is noted in the example.

REFERENCE EXAMPLE 1

γ-type manganese dioxide was synthesized as follows. A hot aqueous solution mixture (60° C.) of 1N-manganese sulfate (II) and 0.2N-sulfuric acid was electrolyzed under a condition of current density 3.0 A/dm$^2$ using an anode of platinum to form electrolytic manganese dioxide on the electrode. It was separated from the electrode and sufficiently washed with water to remove the attached electrolyte. Thereafter, it was neutralized using a 10% solution of NaHCO$_3$. Then it was stirred in a 5% solution of NH$_4$Cl as a peptization inhibitor at a temperature of 60° C. for 1 hour, and suction filtration was repeatedly carried out several times to reduce the S content in the sample to 0.06 wt % or less. Then, it was dried in a constant-temperature bath at 80° to 100° C. to obtain $\gamma$-type manganese dioxide.

REFERENCE EXAMPLE 2

$\beta$-type manganese dioxide was synthesized by heating manganese sulfate (II) hexahydrate in air at 150° to 190° C. for 2 to 3 days, and thereafter washing with boiling diluted nitric acid and then with boiling water, and further heating at a temperature of 450° to 500° C.

EXAMPLE 1 AND COMPARATIVE EXAMPLE 1

Ru-Na-S/MnO$_2$ catalyst (1) was prepared as follows. As manganese oxide, commercially available amorphous MnO$_2$ (guaranteed reagent, surface area 150.9 m$^2$/g) which did not show a diffraction pattern in X-ray diffractiometry was used.

30 g of the amorphous MnO$_2$ powder was stirred in 80 ml of an aqueous solution of sulfuric acid having a pH of 4.8 at room temperature (about 25° C.) for about 24 hours. After it was filtered and dried, it was immersed in water (80 ml). A concentrated aqueous solution of NaOH was added dropwise to control the pH at 9.3. After stirring for about 24 hours, it was dried in an oven at 90° to 100° C. 22.1 g of the Na-S/MnO$_2$ mixture prepared as described above was immersed in a solution prepared by dissolving 2.28 g of ruthenium chloride in 10 ml of a mixture of equal volumes of water and ethanol. After standing for about 24 hours, the solvent was removed under a nitrogen stream and the residue was dried in an oven at 90° to 100° C. to prepare a catalyst (1).

The catalyst (1) prepared as described above contained 0.45 wt % of Na, 0.26 wt % of S and 4.0 wt % of Ru. 2 ml (2.60 g) of this catalyst was placed in a reactor, and it was subjected to reduction processing at 400° C. for 2 hours under a hydrogen gas atmosphere. Subsequently, it was cooled to a temperature of lower than the reaction temperature (about 100° C.) in a hydrogen gas. Thereafter, a reaction gas consisting of carbon monoxide and hydrogen (molar ratio of H$_2$/CO=1) was fed to the catalyst layer as a cocurrent downstream, and catalytic performance was evaluated.

Reaction conditions and composition of the product are shown in Table 1.

For comparison, a Ru-Na/MnO$_2$ catalyst (3) which was not subjected to processing with the aqueous solution of H$_2$SO$_4$, a Ru-S/MnO$_2$ catalyst (2) which was not subjected to processing with an aqueous solution of NaOH, and a Ru/MnO$_2$ catalyst (4) which was not subjected to processing with either of the aqueous solutions of H$_2$SO$_4$ or NaOH were prepared in the same manner as for the above described catalyst (1), and they were analogously evaluated. The results are shown in Table 1.

It should be noted that, in the case of the Ru-Na-S/MnO$_2$ catalyst, the amount of methane formed is very low, the ratio of olefin/paraffin in the C$_2$ fraction is remarkably improved, and the selectivity for C$_2$ to C$_4$ lower olefins is particularly high, as compared with the cases of the catalysts which do not contain alkali metal, sulfur, or both of them.

TABLE 1

| Catalyst Composition | Reaction conditions | | | CO conversion (%) | Selectivity | | Distribution of hydrocarbons formed (wt %) | | | | | | | Ratio of C$_2^=$/C$_2^-$ | Amount of C$_2$ to C$_4$ formed |
|---|---|---|---|---|---|---|---|---|---|---|---|---|---|---|---|
| | Temperature (°C.) | Pressure (kg/cm$^2$ G) | GHSV (hr$^{-1}$) | | CO$_2$ (%) | Hydrocarbon (%) | C$_1$ | C$_2$ | C$_3$ | C$_4$ | C$_5$ | C$_6$ | C$_7$ | | |
| Example 1: | | | | | | | | | | | | | | | |
| (1) 4% Ru—0.45% Na—0.26% S/MnO$_2$ | 400 | 0 | 1200 | 29.1 | 24.1 | 75.9 | 17.9 | 45.0 | 26.6 | 7.4 | 2.7 | 0.3 | 0.1 | 32.40 | 79.0 |
| (1) 4% Ru—0.45% Na—0.26% S/MnO$_2$ | 400 | 9.3 | 3000 | 38.8 | 35.5 | 64.5 | 25.4 | 29.8 | 25.6 | 11.0 | 4.8 | 2.3 | 1.1 | 2.03 | 66.4 |
| Comparative Example 1: | | | | | | | | | | | | | | | |
| (2) 4% Ru—0.26% S/MnO$_2$ | 400 | 0 | 1200 | 24.8 | 23.8 | 76.2 | 59.5 | 27.8 | 10.4 | 1.8 | 0.4 | 0.1 | 0 | 0.61 | 39.9 |
| (3) 4% Ru—0.51% Na/MnO$_2$ | 400 | 0 | 1200 | 43.2 | 29.8 | 70.2 | 46.8 | 31.8 | 17.2 | 3.3 | 0.8 | 0.1 | 0 | 0.55 | 52.3 |
| (4) 4% Ru/MnO$_2$ | 400 | 0 | 1200 | 45.2 | 33.6 | 66.4 | 57.5 | 31.9 | 8.6 | 1.2 | 0.6 | 0.2 | 0 | 0.1 | 41.7 |
| (4) 4% Ru/MnO$_2$ | 400 | 11.5 | 3000 | 50.2 | 24.1 | 75.9 | 42.5 | 25.9 | 18.9 | 7.5 | 3.1 | 1.5 | 0.6 | 0.1 | 52.3 |

Notes:
(1) The ratio of C$_2^=$/C$_2^-$ shows the ratio of ethylene/ethane (wt/wt) formed. Hereinafter, it has the same meaning.
(2) The amount of C$_2$ to C$_4$ formed shows the total of C$_2$, C$_3$, and C$_4$ in the distribution of the product. Hereinafter, it has the same meaning.
(3) 4% Ru—0.45% Na—0.26% S/MnO$_2$ in Catalyst (1) means the catalyst which consists of 4.0 wt % of Ru, 0.45 wt % of Na, 0.26 wt % of S and the balance of MnO$_2$. The same applies to the subsequent examples and tables.
(4) Oxygen-containing compounds are formed. However, since the amount of them is very small, selectivity for them is neglected. The same applied to the subsequent examples and tables.

EXAMPLE 2 AND COMPARATIVE EXAMPLE 2

Ru-containing catalysts (5), (6), (7) and (8) prepared using various manganese oxides containing the sulfur component and alkali metal which were supported by adjusting pH in the same manner as that for the catalyst (1) of Example 1 (manganese oxides used: $\gamma$-MnO$_2$ in Reference Example 1 (surface area 223.1 m$^2$/g), commercially available $\beta$-MnO$_2$ (guaranteed reagent, high degree of crystallinity, surface area 10.5 m$^2$/g), Mn$_2$O$_3$ (guaranteed reagent, surface area 50.3 m$^2$/g) and Mn$_3$O$_4$ (guaranteed reagent, surface area 18.3 m$^2$/g)), were used for carrying out the reaction. The results are shown in Table 2.

In the example of the present invention, it is understood that the amount of methane formed is small, and particularly, the ratio of olefin/paraffin in the C$_2$ fraction and the amount of $C_2$ to $C_4$ formed are improved in manganese oxide type catalysts (5), (6), (7) and (8), as compared with catalysts (9), (10), (11) and (12), respectively, in comparative example which do not contain alkali metal and the S component, and that Ru/manganese oxide type catalysts containing the alkali metal and S show an excellent effect of forming lower olefins.

using the catalysts (14) and (15) which do not contain both alkali metal and S. The catalyst (14) is different from the catalyst (15) in that the catalyst (14) was prepared using MnO clacined in air at 550° C. for 8 hours, and the catalyst (15) was prepared using MnO which was not calcined. The catalysts (13) and (14) prepared using MnO calcined in air form a remarkably small amount of methane as compared with the Ru/MnO catalyst (15).

TABLE 2

| | | Reaction conditions | | | Selectivity | | Distribution of hydro carbons formed (wt %) | | | | | | | Ratio of $C_2^=/$ $C_2^-$ | Amount of $C_2$ to $C_4$ formed |
|---|---|---|---|---|---|---|---|---|---|---|---|---|---|---|---|
| Catalyst | Composition | Temperature (°C.) | Pressure (kg/cm² G) | GHSV (hr⁻¹) | CO conversion (%) | $CO_2$ (%) | Hydrocarbon (%) | $C_1$ | $C_2$ | $C_3$ | $C_4$ | $C_5$ | $C_6$ | $C_7$ | | |
| Example 2: | | | | | | | | | | | | | | | | |
| (5) | 4% Ru—0.51% Na—0.21% S/MnO₂ (γ-type) | 400 | 0 | 1500 | 20.2 | 24.3 | 75.7 | 17.9 | 45.0 | 26.6 | 7.4 | 2.7 | 0.3 | 0.1 | 54.5 | 79.0 |
| (5) | 4% Ru—0.51% Na—0.21% S/MnO₂ (γ-type) | 400 | 10.8 | 2400 | 41.8 | 16.4 | 83.6 | 30.6 | 32.6 | 22.6 | 8.9 | 3.4 | 1.3 | 0.6 | 4.35 | 64.1 |
| (6) | 1% Ru—0.85% K—0.32% S/MnO₂ (β-type) | 400 | 0 | 150 | 14.3 | 27.8 | 72.2 | 72.1 | 21.2 | 5.9 | 0.7 | 0.1 | 0 | 0 | 1.56 | 27.8 |
| (7) | 4% Ru—1.45% Rb—0.25% S/Mn₂O₃ | 400 | 0 | 1500 | 22.2 | 18.6 | 81.4 | 23.4 | 44.7 | 23.9 | 5.6 | 1.9 | 0.4 | 0.1 | 16.55 | 74.2 |
| (8) | 1% Ru—0.33% Na—0.19% S/Mn₃O₄ | 400 | 0 | 150 | 7.6 | 7.7 | 92.3 | 61.6 | 27.4 | 9.0 | 1.4 | 0.5 | 0.1 | 0 | 2.49 | 37.8 |
| Comparative Example 2: | | | | | | | | | | | | | | | | |
| (9) | 4% Ru/MnO₂ (γ-type) | 400 | 0 | 1500 | 22.7 | 30.2 | 69.8 | 27.3 | 38.5 | 23.2 | 8.2 | 2.3 | 0.4 | 0.1 | 25.70 | 69.9 |
| (9) | 4% Ru/MnO₂ (γ-type) | 400 | 12.1 | 2400 | 44.6 | 19.7 | 80.3 | 34.4 | 28.3 | 21.0 | 9.4 | 4.1 | 1.9 | 0.9 | 0.98 | 58.7 |
| (10) | 1% Ru/MnO₂ (β-type) | 400 | 0 | 150 | 15.7 | 20.2 | 79.8 | 82.6 | 13.8 | 2.1 | 1.4 | 0.1 | 0 | 0 | 0.21 | 17.3 |
| (11) | 4% Ru/Mn₂O₃ | 400 | 0 | 1500 | 25.5 | 20.7 | 79.3 | 48.7 | 32.4 | 15.3 | 3.0 | 0.6 | 0 | 0 | 2.09 | 50.7 |
| (12) | 1% Ru/Mn₃O₄ | 400 | 0 | 150 | 9.7 | 9.8 | 90.2 | 80.8 | 13.9 | 4.5 | 0.7 | 0.1 | 0 | 0 | 1.00 | 19.1 |

TABLE 3

| | | Reaction conditions | | | | Selectivity | | Distribution of hydrocarbons formed (wt %) | | | | | | | Ratio of $C_2^=/$ $C_2^-$ | Amount of $C_2$ to $C_4$ formed |
|---|---|---|---|---|---|---|---|---|---|---|---|---|---|---|---|---|
| Catalyst | Composition | Temperature (°C.) | Pressure (kg/cm² G) | GHSV (hr⁻) | CO conversion (%) | $CO_2$ (%) | Hydrocarbon (%) | $C_1$ | $C_2$ | $C_3$ | $C_4$ | $C_5$ | $C_6$ | $C_7$ | | | |
| Example 3: | | | | | | | | | | | | | | | | | |
| (13) | 2% Ru—0.41% Na—0.26% S/550 MnO | 400 | 0 | 300 | 28.8 | 22.1 | 77.9 | 25.5 | 41.8 | 25.7 | 5.1 | 1.2 | 0.7 | 0 | 16.23 | 72.6 | |
| (13) | 2% Ru—0.41% Na 0.26% S/550 MnO | 400 | 0 | 600 | 18.0 | 17.3 | 82.7 | 24.3 | 46.7 | 22.5 | 4.7 | 1.2 | 0.6 | 0 | 27.05 | 73.9 | |
| Comparative Example 3: | | | | | | | | | | | | | | | | | |
| (14) | 2% Ru/550 MnO | 400 | 0 | 300 | 30.8 | 5.4 | 94.6 | 30.3 | 45.0 | 20.1 | 3.7 | 0.8 | 0.1 | 0 | 0.42 | 68.8 | |
| (15) | 2% Ru/MnO | 400 | 0 | 300 | 18.4 | 1.9 | 98.1 | 43.4 | 37.7 | 15.4 | 2.9 | 0.6 | 0 | 0 | 0.97 | 56.0 | |

EXAMPLE 3 AND COMPARATIVE EXAMPLE 3

20.0 g of a manganese oxide powder obtained by calcining a comercially available MnO powder (guaranteed reagent, surface area 11.8 m²/g) in air at 550° C. for 8 hours was processed with aqueous solutions of $H_2SO_4$ and NaOH in the same manner as for the catalyst (1) in Example 1. After supporting Na and S components, ruthenium was applied to prepare a catalyst (13), and the reaction was carried out using it. The results are shown in Table 3. When calcining was carried out as described above, MnO changed color from initial yellowish green to grayish brown. This change meant that a part of the MnO was converted into $Mn_2O_3$ and/or $MnO_2$.

It should be noticed that, in the example of the present invention, the selectivity for $C_2$ to $C_4$ lower olefins is remarkably improved as compared with the case of

EXAMPLE 4 AND COMPARATIVE EXAMPLE 4

A Ru-K-S/β-MnO₂ type catalyst was prepared as follows. As manganese oxide, β-MnO₂ synthesized by the method of Reference Example 2 was used (which had slightly inferior crystallinity; surface area 34.9 m²/g). 100 g of this β-MnO₂ powder was immersed in 100 ml of an aqueous solution containing 0.61 g of KSCN. After standing at room temperature for about 24 hours, the solvent was removed by a water aspirator and drying was carried out at 80° to 100° C. in an oven. To 10 g of the K-S/β-MnO₂ mixture prepared as described above, 6 ml of a solution containing 0.45 g of ruthenium chloride in a mixture of water-ethanol in equal volume was added dropwise. After standing at room temperature for about 24 hours, the solvent was removed under a nitrogen stream, and drying was carried out at 90° to 110° C. in an oven to obtain a catalyst (16). The catalyst (16) prepared as described above contained 0.24 wt % of K, 0.2 wt % of S and 2.0 wt % of Ru. A catalyst (17) containing potassium and sulfur was prepared by the same manner as that for the catalyst (16), except that $K_2SO_4$ was used as the K-S containing compound instead of KSCN. Using these catalysts, the reaction was carried out by the same manner as in Example 1. Reaction conditions and results are shown in Table 4. It is understood from the results shown in Table 4 that formation of methane is remarkably restricted and selectivity for $C_2$ to $C_4$ lower olefins is remarkably improved, even if a compound containing both of alkali metal and sulfur is added to manganese oxide.

shown as a synergistic effect of alkali metal and sulfur as shown in Example 1.

TABLE 5

| | Catalyst Composition | Reaction conditions | | | CO conversion (%) | Selectivity | | Distribution of hydrocarbons formed (wt %) | | | | | | | Ratio of $C_2^=$/$C_2^-$ | Amount of $C_2$ to $C_4$ formed |
|---|---|---|---|---|---|---|---|---|---|---|---|---|---|---|---|---|
| | | Temperature (°C.) | Pressure (kg/cm² G) | GHSV (hr⁻¹) | | $CO_2$ (%) | Hydrocarbon (%) | $C_1$ | $C_2$ | $C_3$ | $C_4$ | $C_5$ | $C_6$ | $C_7$ | | |
| | Example 5: | | | | | | | | | | | | | | | |
| (19) | 2% Ru—2.2% K—0.45% S/γ-$MnO_2$ | 400 | 0 | 1200 | 15.0 | 12.5 | 87.5 | 18.1 | 46.4 | 24.9 | 7.3 | 2.9 | 0.4 | 0 | 51.56 | 78.6 |
| (20) | 2% Ru—2.1% K—0.45% S/γ-$MnO_2$ | 400 | 0 | 1200 | 13.5 | 18.3 | 81.7 | 18.8 | 40.7 | 23.3 | 7.8 | 5.0 | 2.8 | 1.6 | 44.1 | 71.8 |

EXAMPLE 6 AND COMPARATIVE EXAMPLE 5

A Ru-Na/$MnO_2$ catalyst (22) was prepared using commercially available amorphous $MnO_2$ (guaranteed reagent, surface area 150.9 m²/g) by the same manner as that for the catalyst (1) shown in Example 1 except that addition of sulfur by processing with an aqueous solution of $H_2SO_4$ was not carried out, and the reaction was conducted using it. After the reaction was carried out under the prescribed reaction conditions, 5 ml portions of $H_2S$ gas were injected 9 times into a reaction gas by a pulse injection process so that a part of the surface of the catalyst was poisoned. Using this catalyst (21), the

TABLE 4

| | Catalyst Composition | Reaction conditions | | | CO conversion (%) | Selectivity | | Distribution of hydrocarbons formed (wt %) | | | | | | | Ratio of $C_2^=$/$C_2^-$ | Amount of $C_2$ to $C_4$ formed |
|---|---|---|---|---|---|---|---|---|---|---|---|---|---|---|---|---|
| | | Temperature (°C.) | Pressure (kg/cm² G) | GHSV (hr⁻¹) | | $CO_2$ (%) | Hydrocarbon (%) | $C_1$ | $C_2$ | $C_3$ | $C_4$ | $C_5$ | $C_6$ | $C_7$ | | |
| | Example 4: | | | | | | | | | | | | | | | |
| (16) | 2% Ru—0.24% K—0.2% S/β-$MnO_2$ | 400 | 0 | 1200 | 29.3 | 44.2 | 55.7 | 19.6 | 33.4 | 28.7 | 11.7 | 5.0 | 1.2 | 0.4 | 7.82 | 73.8 |
| (17) | 2% Ru—0.5% K—(0.2% S/β-$MnO_2$ | 400 | 0 | 1200 | 30.3 | 41.0 | 59.0 | 16.4 | 33.3 | 28.3 | 11.6 | 5.3 | 4.4 | 0.7 | 5.18 | 73.2 |
| | Comparative Example 4 | | | | | | | | | | | | | | | |
| (18) | 2% Ru/β-$MnO_2$ | 400 | 0 | 1200 | 32.5 | 35.6 | 64.4 | 65.4 | 23.7 | 8.2 | 1.7 | 0.8 | 0.1 | 0 | 1.71 | 33.6 |

EXAMPLE 5

12 g of γ-type $MnO_2$ prepared according to the process shown in Reference Example 1 (which was prepared in a different batch from that of the γ-type $MnO_2$ used in Example 2; surface area 196 m²/g) was immersed in 80 ml of an aqueous solution of sulfuric acid having pH 3.9, and it was stirred at room temperature for 15 hours. After it was filtered, washed with water and dried, it was immersed in 12 ml of an aqueous solution containing 0.51 g of KCl. After standing for about 24 hours, the solvent was removed by a water-aspirator, and drying was carried out at 90° to 110° C. in an oven. The K-S/γ-$MnO_2$ mixture prepared as described above was impregnated with ruthenium chloride by the same manner as shown in Example 1 to obtain a Ru-K-S/γ-$MnO_2$ catalyst (19). A catalyst (20) was prepared by the same manner as in Catalyst (19), except that $KNO_3$ was used instead of KCl so that anion of alkali metal salt was changed. Using these catalysts, the reaction was carried out by the same manner as in Example 1. The reaction conditions and results thereof are shown in Table 5. It is obvious from the results of Table 5 that neither distribution of the reaction product nor olefin selectivity is influenced by the alkali metal source, if the anion of alkali metal salt is changed, and the selectivity thereof is reaction was carried out. Results are shown in Table 6. Incorporation of sulfur on the catalyst can be carried out by various processes. Conversion, distribution of the product, and olefin selectivity were nearly equal in the case of using the catalyst (21) of this example obtained by directly introducing a gaseous sulfur compound together with the reaction gas and in the case of using the catalysts obtained by introducing a sulfur component as a sulfuric acid radical or SCN ion, etc., at preparation of the catalyst (refer to Examples 1 to 5). Accordingly, the process which comprises introducing a gaseous sulfur compound into a reaction system, as shown in this example, is a simple process in the viewpoint of preparation of the catalyst. As is shown in Table 6, selectivity for $C_2$ to $C_4$ lower olefins, and particularly the ratio of olefin/paraffin in the $C_2$ fraction are remarkably improved in case of using the catalyst (21) of the present invention as compared with the case of using the catalyst (22) to which $H_2S$ was not added.

Further, it should be noticed that the catalyst of the present invention has excellent sulfur resistance and olefin selectivity was improved by the sulfurization processing according to the present invention as compared with the Ru/γ-$Al_2O_3$ catalyst (24) in comparative example. The catalyst (23) was prepared by sulfurizing the catalyst (24) with 5 ml portions of $H_2S$ gas 4 times, i.e., for a total of 20 ml. When the catalyst (23) used, CO conversion deteriorated.

distribution of the product followed the Schultz-Flory law, the ratio of olefin/paraffin in the product was high,

TABLE 6

| Catalyst Composition | Reaction conditions | | | CO conversion (%) | Selectivity | | Distribution of hydrocarbons formed (wt %) | | | | | | | Ratio of $C_2^=$/$C_2^-$ | Amount of $C_2$ to $C_4$ formed |
|---|---|---|---|---|---|---|---|---|---|---|---|---|---|---|---|
| | Temperature (°C.) | Pressure (kg/cm² G) | GHSV (hr$^{-1}$) | | $CO_2$ (%) | Hydrocarbon (%) | $C_1$ | $C_2$ | $C_3$ | $C_4$ | $C_5$ | $C_6$ | $C_7$ | | |
| Example 6: | | | | | | | | | | | | | | | |
| (21) 1% Ru—0.28% Na—0.37% S/$MnO_2$ | 400 | 0 | 150 | 34.8 | 25.6 | 74.4 | 20.3 | 45.6 | 24.3 | 6.0 | 2.6 | 1.1 | 0.1 | 16.51 | 75.9 |
| Comparative Example 5: | | | | | | | | | | | | | | | |
| (22) 1% Ru—0.28% Na/$MnO_2$ | 400 | 0 | 150 | 35.6 | 17.7 | 82.2 | 30.0 | 39.7 | 22.4 | 5.6 | 1.3 | 0.9 | 0.1 | 0.49 | 67.7 |
| (23) 1% Rn—0.21% S/$\gamma$-$Al_2O_3$ | 400 | 0 | 150 | 2.4 | 1.8 | 98.2 | 70.5 | 24.3 | 3.4 | 1.2 | 0.5 | 0.1 | 0 | 2.48 | 28.9 |
| (24) 1% Ru/$\gamma$-$Al_2O_3$ | 400 | 0 | 150 | 42.1 | 2.1 | 97.9 | 99.9 | 0.02 | 0.007 | 0 | 0 | 0 | 0 | 0 | 0.03 |

EXAMPLE 7 AND COMPARATIVE EXAMPLE 6

$\gamma$-type $MnO_2$ prepared according to the process shown in Reference Example 1 (surface area 223.1 m²/g) was immersed in 80 ml of an aqueous solution of sulfuric acid having pH 5.2, and it was stirred at room temperature for 25 hours. After it was filtered and dried, it was immersed in water (80 ml), and a concentrated aqueous solution of NaOH was added dropwise thereto to adjust the pH to 8.5. The resulting Na-S/$\gamma$-$MnO_2$ mixture was processed with a solution of ruthenium chloride in a mixture of water-ethanol in equal volumes so as to support 1 wt % as the metal per the catalyst weight. After the solvent was removed and drying was carried out in an oven, the product was subjected to calcining processing in the air by means of an electric oven at 450° C. for 24 hours to produce a catalyst (25). This catalyst was placed in a reactor and subjected to reduction processing in the same manner as in Example 1, and the reaction was carried out using it. Reaction conditions and distribution and composition of the product are shown in Table 7. When the catalyst was subjected to calcining processing in air after application of ruthenium, distribution of the product greatly changed, whereby it became advantageous for forming a high boiling point fraction, as compared with the case of the catalyst (5) in Example 2. Further, though the as compared with the case of using the Ru/$\gamma$-$Al_2O_3$ catalyst (26) (which was calcined at 450° C. for 24 hours) shown as a comparative example. Further, it was understood that $\alpha$-olefin content in the olefin composition obtained was 90% or more and the catalyst was advantageous in olefin selectivity, particularly with respect to formation of higher $\alpha$-olefins, at high temperature under high pressure.

TABLE 7

| Catalyst Composition | Reaction conditions | | | CO conversion (%) | Selectivity | | Distribution of hydrocarbons formed (wt %) | | | |
|---|---|---|---|---|---|---|---|---|---|---|
| | Temperature (°C.) | Pressure (kg/cm² G) | GHSV (hr$^{-1}$) | | $CO_2$ (%) | Hydrocarbon (%) | $C_1$ | $C_2$ | $C_3$ | $C_4$ |
| Example 7: | | | | | | | | | | |
| (25) 1% Ru—0.48% Na—0.29% S/$\gamma$-$MnO_2$ | 330 | 10 | 1200 | 46.7 | 8.3 | 91.7 | 11.7 | 12.4 | 17.5 | 14.4 |
| (Ratio of olefin/paraffin) | | | | | | | | 2.02 | 5.06 | 4.81 |
| Comparative Example 6: | | | | | | | | | | |
| (26) 1% Ru/$\gamma$-$Al_2O_3$ | 330 | 10 | 1200 | 48.5 | 2.7 | 97.3 | 68.9 | 13.0 | 11.8 | 3.9 |
| (Ratio of olefin/paraffin) | | | | | | | | 0.02 | 0.3 | 0.19 |

| Catalyst Composition | Distribution of hydrocarbons formed (wt %) | | | | | | | | | | | | | |
|---|---|---|---|---|---|---|---|---|---|---|---|---|---|---|
| | $C_5$ | $C_6$ | $C_7$ | $C_8$ | $C_9$ | $C_{10}$ | $C_{11}$ | $C_{12}$ | $C_{13}$ | $C_{14}$ | $C_{15}$ | $C_{16}$ | $C_{17}$ | $C_{18}$ |
| Example 7: | | | | | | | | | | | | | | |
| (25) 1% Ru—0.48% Na—0.29% S/$\gamma$-$MnO_2$ | 11.9 | 6.9 | 4.8 | 4.6 | 2.9 | 2.6 | 1.8 | 1.6 | 1.5 | 1.4 | 1.2 | 1.0 | 0.8 | 1.0 |
| (Ratio of olefin/paraffin) | 4.66 | 4.31 | 4.14 | 3.97 | 3.63 | 3.42 | 3.19 | 2.73 | 2.15 | 1.54 | 1.08 | 0.62 | 0.42 | |
| Comparative Example 6: | | | | | | | | | | | | | | |
| (26) 1% Ru/$\gamma$-$Al_2O_3$ | 1.5 | 0.6 | 0.2 | 0.1 | 0 | 0 | 0 | 0 | 0 | 0 | 0 | 0 | 0 | 0 |
| (Ratio of olefin/paraffin) | 0.15 | 0.10 | 0.04 | 0.02 | | | | | | | | | | |

Note:
$C_{18+}$ means the amount of $C_{18}$ and higher hydrocarbons formed.

As shown in the above described Examples 1 to 7, according to the present invention, hydrocarbons rich in olefins are obtained from a synthesis gas in good selectivity and yield when a carbon monoxide reduction catalyst comprising ruthenium, manganese oxide, alkali metal, and sulfur as components is used.

EXAMPLE 8 AND COMPARATIVE EXAMPLE 7

Preparation of carbon monoxide reduction catalyst:

A carbon monoxide reduction catalyst comprising ruthenium, manganese oxide, alkali metal, and sulfur components was prepared as follows.

Manganese oxide obtained in Reference Example 1 was ground by means of an agate mortar to produce a fine powder. After it was immersed in an aqueous solution of sulfuric acid so that the sulfur content became 0.5 wt % based on the whole weight of the carbon monoxide reduction catalyst, it was dried at 110° C. for 3 hours. After it was immersed again in an aqueous solution of potassium hydroxide so that the potassium content became 1.35 wt % based on the total weight of the carbon monoxide reduction catalyst, it was dried at 110° C. for 3 hours, and it was subjected to calcining processing at 450° C. for 3 hours to prepare a mixture composed of manganese oxide, alkali metal, and sulfur components. After this mixture was immersed in an aqueous solution of ruthenium chloride so that the ruthenium content became 2.0 wt % based on the total weight of the carbon monoxide reduction catalyst, it was dried at 120° C. for 3 hours, and subsequently calcined at 450° C. for 8 hours to obtain a carbon monoxide reduction catalyst A (abbreviation for 2% Ru-1.35% K-0.5% S/MnO$_2$).

Preparation of crystalline zeolite:

ZSM-5 type zeolite was synthesized as follows.

Solution A, wherein 17.1 g of aluminium sulfate, 18.5 g of concentrated sulfuric acid and 22.6 g of tetrapropylammonium bromide were dissolved in 180 g of water, Solution B, wherein 207 g of water glass No. 3 (silica 28.9%) was dissolved in 140 g of water, and Solution C wherein 78.8 g of sodium chloride was dissolved in 320 g of water were prepared. Solution C was vigorously stirred and Solution A and Solution B were added dropwise at the same time and mixed. Then, the mixture was put in a 1 l stainless steel autoclave. It was stirred at 100-150 rpm, and the temperature was gradually raised. The reaction was carried out at 160° C. for 20 hours. Thereafter, the reaction mixture was cooled slowly. The resulting fine white crystals were filtered off and washed with water. This operation was repeatedly carried out until the pH of washing water became about 8. After dried at 120° C., it was calcined in air at 550° C. for 6 hours. In order to convert into H-type zeolite, ion-exchange was carried out at a temperature of 80° to 90° C. using a 2N aqueous solution of ammonium chloride in an amount of 5 ml per gram of zeolite. After filtered off and washed with water, the same processing was repeatedly carried out 5 times using a fresh aqueous solution of ammonium chloride. Thereafter, it was washed with water and dried at 120° C. for 3 hours. It was then calcined again in air at 550° C. for 6 hours to obtain H-type ZSM-5 type zeolite.

Catalyst of the present example:

Equal volumes of the above described carbon monoxide reduction catalyst A and the above described H-type ZSM-5 zeolite were sufficiently mixed in a mortar, and the mixture was then molded in the size of 1 to 2 mm to obtain a catalyst (27) (ruthenium 1.6 wt %, potassium 1.0 wt % and sulfur 0.4 wt %, based on the whole weight of the catalyst; abbreviation: 1.6% Ru-1.0% K-0.4% S/MnO$_2$+ZSM-5).

Comparative catalyst:

A carbon monoxide reduction catalyst which was composed of ruthenium, manganese oxide, and alkali metal component, that which was composed of ruthenium, manganese oxide, and sulfur component and that which was composed of ruthenium, and manganese oxide component were prepared, respectively, in the same manner as that for preparing the above described carbon monoxide reduction catalyst A, except that processing with an aqueous solution of sulfuric acid, processing with an aqueous solution of potassium hydroxide and processing with aqueous solutions of both sulfuric acid and potassium hydroxide were not carried out, respectively. Then, catalysts (28), (29) and (30) were prepared, respectively, using zeolite in the same ratio of mixing by the same manner as those for the catalyst (27).

Further, a carbon monoxide reduction catalyst (31) composed of rethenium, and manganese oxide component which was not mixed with zeolite was prepared.

Reaction:

The prepared catalyst was placed in a reactor. After it was previously reduced with hydrogen at 400° C. for 2 hours, the reaction was carried out using a synthesis gas composed of carbon monoxide and hydrogen (H$_2$/CO=1) and results shown in Table 8 were obtained. The amount of the catalyst charged was 4 ml (3.39 g) in case of catalysts (27), (28), (29), and (30) and 2 ml in case of the catalyst (31).

In the case of using the catalyst (27) prepared by mixing the carbon monoxide reduction catalyst composed of ruthenium, manganese oxide, alkali metal, and sulfur component and H-ZSM-5 type zeolite, the amount of methane formed was sufficiently small, formation of the gasoline fraction of C$_5$ to C$_{12}$ hydrocarbons was remarkably improved, and the aromatic component content in the formed hydrocarbons was high, as compared with the case of using catalysts which were lacking in either the alkali metal or sulfur component, or both of them. Further, it should be particularly noted that since the methane formation rate is low in a wide temperature range, a gasoline fraction having high quality can be obtained in a high yield.

TABLE 8

| | | Reaction conditions | | | Selectivity | | Distribution of hydrocarbon product (wt %) | | | | Aromatic component content |
|---|---|---|---|---|---|---|---|---|---|---|---|
| Catalyst Composition | Temperature (°C.) | Pressure (kg/cm$^2$ G) | GHSV (hr$^{-1}$) | CO conversion (%) | CO$_2$ (%) | Hydrocarbon (%) | C$_1$ | C$_2$ to C$_4$ | C$_5$ to C$_{12}$ | C$_{13+}$ | (wt %) |
| Example 8: | | | | | | | | | | | |
| (27) 1.6% Ru—1.0% K—0.4% S/γ-MnO$_2$ + ZSM-5 | 300 | 10.3 | 600 | 47.6 | 0.8 | 99.2 | 5.7 | 9.7 | 83.3 | 1.3 | 28.9 |
| (27) 1.6% Ru—1.0% K—0.4% S/γ-MnO$_2$ + ZSM-5 | 270 | 10.0 | 600 | 35.6 | 0.8 | 99.2 | 4.5 | 15.3 | 79.4 | 0.8 | 18.5 |
| (27) 1.6% Ru—1.0% K—0.4% S/γ-MnO$_2$ + ZSM-5 | 330 | 10.0 | 600 | 62.1 | 21.0 | 79.0 | 10.1 | 25.0 | 64.6 | 0.3 | 27.7 |
| Comparative Example 7: | | | | | | | | | | | |
| (28) 1.6% Ru—1.0% K/γ-MnO$_2$ + ZSM-5 | 300 | 10.1 | 600 | 48.2 | 1.5 | 98.5 | 18.7 | 47.4 | 32.4 | 1.5 | 12.3 |
| (29) 1.6% Ru—0.4% S/γ-MnO$_2$ + ZSM-5 | 300 | 10.2 | 600 | 48.0 | 1.2 | 98.8 | 24.5 | 38.3 | 35.8 | 1.4 | 10.1 |
| (30) 1.6% Ru/γ-MnO$_2$ + ZSM-5 | 300 | 10.0 | 600 | 50.8 | 2.1 | 97.9 | 20.7 | 45.4 | 32.9 | 1.0 | 11.7 |

TABLE 8-continued

| Catalyst Composition | Reaction conditions | | | CO conversion (%) | Selectivity | | Distribution of hydrocarbon product (wt %) | | | | Aromatic component content (wt %) |
|---|---|---|---|---|---|---|---|---|---|---|---|
| | Temperature (°C.) | Pressure (kg/cm² G) | GHSV (hr$^{-1}$) | | $CO_2$ (%) | Hydrocarbon (%) | $C_1$ | $C_2$ to $C_4$ | $C_5$ to $C_{12}$ | $C_{13+}$ | |
| (31) 2.0% Ru/γ-$MnO_2$ | 300 | 10.5 | 1200 | 49.3 | 1.8 | 98.2 | 13.1 | 42.2 | 36.2 | 8.5 | 0.0 |

Note:
Aromatic component content means the content in hydrocarbons formed. Hereinafter, it shows the same meaning.

EXAMPLE 9

A catalyst (32) was prepared in the same manner as that for preparing the catalyst (27) in Example 8 except that calcining was not carried out in case of preparing the carbon monoxide reduction catalyst A used for the catalyst (27). After it was reduced with hydrogen at 400° C., a synthesis gas of a ratio $H_2$/CO of 0.5/1 (molar ratio) was allowed to pass through the catalyst charged in an amount of 4 ml to carry out the reaction, and the results shown in Table 9 were obtained.

EXAMPLE 10

Crystalline iron silicate and crystalline gallium silicate were prepared in the same manner as that for preparing the zeolite catalyst of the catalyst (27), except that 5.10 g of ferric chloride ($FeCl_3 \cdot 6H_2O$) and 8.10 g of gallium sulfate, respectively, were used, instead of the 17.1 g of aluminium sulfate in the case of preparing the crystalline zeolite for incorporating in the catalyst (27) in Example 8, As Y-type zeolite commercially available SK-41 produced by Union Carbide Co. was used. These crystalline zeolite catalysts were mixed with the same carbon monoxide reduction catalyst A as that for incorporating in the catalyst (27) in Example 8, in equal volumes, to prepare catalysts (33), (34), and (35), respectively. Using these catalysts, the reaction was carried out similarly to Example 8. The results are shown in Table 9.

TABLE 9

| Catalyst Composition | Reaction conditions | | | CO conversion (%) | Selectivity | | Distribution of hydrocarbon product (wt %) | | | | Aromatic component content (wt %) |
|---|---|---|---|---|---|---|---|---|---|---|---|
| | Temperature (°C.) | Pressure (kg/cm² G) | GHSV (hr$^{-1}$) | | $Co_2$ (%) | Hydrocarbon (%) | $C_1$ | $C_2$ to $C_4$ | $C_5$ to $C_{12}$ | $C_{13+}$ | |
| (32) 1.6% Ru—1.0% K—0.4% S/$MnO_2$ + ZSM-5 Example 10: | 360 | 4.7 | 300 | 34.2 | 4.0 | 96.0 | 16.2 | 16.3 | 67.5 | 0 | 31.1 |
| (33) 1.6% Ru—1.0% K—0.4% S/γ-$MnO_2$ + Fe silicate | 300 | 10.0 | 600 | 47.3 | 0.9 | 99.1 | 6.9 | 12.2 | 80.3 | 0.6 | 20.2 |
| (34) 1.6% Ru—1.0% K—0.4% S/γ-$MnO_2$ + Ga silicate | 300 | 10.0 | 600 | 48.2 | 1.5 | 98.5 | 7.0 | 11.5 | 80.9 | 0.6 | 20.4 |
| (35) 1.6% Ru—1.0% K—0.4% S/γ-$MnO_2$ + SK-41 | 300 | 10.0 | 600 | 47.7 | 1.8 | 98.2 | 8.3 | 25.3 | 65.2 | 1.2 | 12.6 |

As be shown in Examples 8 to 10, when catalysts obtained by mixing the carbon monoxide reduction catalyst composed of ruthenium, manganese oxide, alkali metal and sulfur component with zeolite with zeolite in the present invention are used, hydrocarbons rich in a fraction capable of being utilized as gasoline can be obtained directly from the synthesis gas in a high yield.

While the invention has been described in detail and with reference to specific embodiments thereof, it will be apparent to one skilled in the art that various changes and modifications can be made therein without departing from the spirit and scope thereof.

What is claimed is:

1. A process for producing hydrocarbons which comprises bringing a gas mixture comprising hydrogen and carbon monoxide into contact with a catalyst comprising at least 5% by weight based on the total catalyst a carbon monoxide reduction catalyst at reaction conditions comprising a pressure of from 0 to 100 kg/cm²G and a temperature of from 100° to 500° C. to produce hydrocarbons, wherein said carbon monoxide reduction catalyst comprises 10 to 99.8 wt % manganese oxide, 0.01 to 8 wt % alkali metal, 0.001 to 3 wt % sulfur, and 0.1 to 50 wt % ruthenium based on the total weight of the carbon monoxide reduction catalyst.

2. A process according to claim 1, wherein the catalyst consists essentially of said carbon monoxide reduction catalyst.

3. A process according to claim 1, wherein the catalyst further comprises crystalline zeolite.

4. A process according to claim 1, wherein the carbon monoxide reduction catalyst additionally contains at least one of a member selected from the group consisting of $TiO_2$, $SiO_2$, $Al_2O_3$, $Cr_2O_3$, $V_2O_5$, $WO_3$, $MoO_3$ and natural clay minerals.

5. A process according to claim 1 wherein the manganese oxide is at least one oxide selected from the group consisting of $MnO_2$, $Mn_2O_3$, $MnO_3O_4$, and MnO.

6. A process according to claim 1, wherein said alkali metal is lithium, sodium, potassium, cesium, or rubidium.

7. A process according to claim 3, wherein the crystalline zeolite is crystalline aluminosilicate or crystalline silicate.

8. A process according to claim 1, wherein the reaction conditions comprise a molar ratio of hydrogen to carbon monoxide of from 0.1/1 to 10/1.

9. A process according to claim 1, wherein the carbon monoxide reduction catalyst contains from 0.05 to 6 wt % alkali metal, from 0.07 to 1.5 wt % sulfur, and from 0.1 to 30 wt % ruthenium.

10. A process according to claim 2, wherein the carbon monoxide reduction catalyst contains from 0.05 to 6 wt % alkali metal, from 0.07 to 1.5 wt % sulfur, and from 0.1 to 30 wt % ruthenium.

11. A process according to claim 3, wherein the carbon monoxide reduction catalyst contains from 0.05 to 6 wt % alkali metal, from 0.07 to 1.5 wt % sulfur, and from 0.1 to 30 wt % ruthenium.

12. A process according to claim 11, wherein the carbon monoxide reduction catalyst contains from 0.5 to 25 wt % ruthenium.

13. A process according to claim 1, wherein the reaction conditions comprise a pressure of from 0 to 30 kg/cm$^2$G, a temperature of from about 200° to 450° C., and a molar ratio of hydrogen to carbon monoxide of from 0.5/1 to 4/1.

14. A process according to claim 2, wherein the reaction conditions comprise a pressure of from 0 to 30 kg/cm$^2$G, a temperature of from about 200° to 450° C., and a molar ratio of hydrogen to carbon monoxide of from 0.5/1 to 4/1.

15. A process according to claim 3, wherein the reaction conditions comprise a pressure of from 0 to 30 kg/cm$^2$G, a temperature of from about 200° to 450° C., and a molar ratio of hydrogen to carbon monoxide of from 0.5/1 to 4/1.

16. A process according to claim 1, wherein the reaction conditions comprise a pressure of from 0 to 20 kg/cm$^2$G, a temperature of from about 250° to 400° C., and a molar ratio of hydrogen to carbon monoxide of from 0.5/1 to 1/1.

17. A process according to claim 1, wherein the carbon monoxide reduction catalyst additionally contains at least one activator selected from the group consisting of magnesium, zinc, copper and iron.

* * * * *